(12) United States Patent
Copland, III et al.

(10) Patent No.: US 6,333,313 B1
(45) Date of Patent: Dec. 25, 2001

(54) CLINICAL USE OF OXYTOCIN ALONE OR IN COMBINATION TO TREAT BONE DISORDERS

(75) Inventors: John A. Copland, III, Houston; Kirk Lorne Ives, Dickinson, both of TX (US); David J. Simmons, St. Louis, MO (US); Melvyn Soloff, Galveston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/430,114

(22) Filed: Oct. 29, 1999

Related U.S. Application Data
(60) Provisional application No. 60/106,134, filed on Oct. 29, 1998.

(51) Int. Cl.$^7$ .................................................. A61K 38/00
(52) U.S. Cl. .............................................................. 514/12
(58) Field of Search ................................................ 514/12

(56) References Cited

PUBLICATIONS

Pettibone et al., "Progress in the development of oxytocin antagonists for use in preterm labor," *Oxytocin*, 395:601–612, 1995.
Williams et al., "Nonpeptide oxytocin antagonists: analogs of L–371,257 with improved potency," *Bioorganic & Medicinal Chemistry Letters*, 9:1311–1316, 1999.
Acog Technical Bulletin, "Induction of Labor," No. 217, Dec. 1995.
Acog Technical Bulletin, "Preterm Labor," No. 206, Jun. 1995.
Chadio and Antoni, "Specific oxytocin agonist stimulates prolactin release but has no effect on inositol phosphate accumulation in isolated rat anterior pituitary cells," *J Mol Endocrinol* 10(2):107–114, 1993.
Cheng et al., "Differentiation of human bone marrow osteogenic stromal cells in vitro: Induction of the osteoblast phenotype by dexamethasone," *Endocrinology*, 134:277–286, 1994.
Civitelli et al., "Connexin43 mediates direct intercellular communication in human osteoblastic cell networks," *J. Clin. Invest.*, 91:1888–1896, 1993.
Copland et al., "Demonstration of functional oxytocin receptors in human breast Hs578T cells and their up–regulation through a PKC–dependent pathway," *Endocrinology*, 140:2258–2267, 1999.
Cort et al., "Effect of oxytocin and its long–acting analog on milk let–down and intramammary pressure in healthy lactating sows;" *Am J Vet Res*, 43(7):1283–5, 1982.
Cort et al., "Actions of oxytocin and a long–acting carba oxytocin analog on the porcine myometrium in vitro and in vivo," *Am J Vet Res*, 40(3):430–2, 1979.
Ferraro and Du Vigneaud "7–D–proline–oxytocin and its deamino analog. Diastereoisomers of oxytocin and deamino–oxytocin," *J Am. Chem. Soc.*, 88(16):3847–50, 1966.
Flint et al., "Stimulation of phosphoinositide hydrolysis by oxytocin and the mechanism by which oxytocin controls prostaglandin synthesis in the ovine endometrium," *Biochem. J.* , 237:797–805, 1986.
Fuchs et al., "Oxytocin receptors and human parturition. A dual role for oxytocin in the initiation of labor," *Science*, 215:1396–1398, 1982.
Gazis et al., "In vivo simultaneous comparison of pressor and uterine responses to a single agonist (oxypressin) in estrous rats," *Can J Physiol Pharmacol*, 65(1):6–11, 1987.
Grazzini et al., "Inhibition of oxytocin receptor function by direct binding of progesterone," *Nature*, 392(2):509–512, 1998.
Hinko and Soloff, "Up–regulation of oxytocin receptors in rabbit amnion by adenosine 3',5'—monophosphate," *Endocrinology*, 132:126–132, 1993.
Hinko and Soloff, "Up–regulation of oxytocin receptors in rabbit amnion by glucocorticoids: Potentiation by cyclic adenosine 3',5'—monophosphate," *Endocrinology*, 133:1511–1519, 1993.
Hruby et al., "[2,4–Diisoleucine]–oxytocin. An analog of oxytocin with natriuretic and diuretic activities," *J Med Chem*, 13(2):185–7, 1970.
Hunter et al., "Effect of carbetocin, a long–acting oxytocin analog on the postpartum uterus," *Clin Pharmacol Ther*, 52(1):60–7, 1992.
Jee and Ma, "The in vivo anabolic actions of prostaglandins in bone," *Bone*, 21:297–304, 1997.
Krejci et al., "Passive avoidance behavior: opposite effects of oxytocin analogs with agonist and antagonist properties," *Regul Pept*, 2(5):285–91, 1981.
Ku et al., "Oxytocin stimulates mymoetrial guanodine triphosphatase and phospholipase–C activities via coupling to Galpha q/11," *Endocrinology*, 136:1509–1515, 1995.
Moore et al., "Oxytocin activates the inositol–phopholipid–protein kinase–C system and stimulates prostaglandin production in human amnion cells," *Endocrinology*, 123:1771–1777, 1988.

(List continued on next page.)

*Primary Examiner*—Theodore J. Criares
(74) *Attorney, Agent, or Firm*—Fulbright & Jaworski LLP

(57) ABSTRACT

The present invention details the use of oxytocin or oxytocin analogs as a novel therapeutic regimen for the treatment of various bone diseases and for assisting in bone remodeling. Oxytocin and oxytocin analogs can be administered alone or in combination with other agents used to treat bone diseases or aid in bone remodeling. In addition, agents which induce endogenous oxytocin release are also contemplated in the present invention for treatment of bone diseases and for assisting in bone remodeling. Diseases and conditions that are contemplated to benefit from the present invention include osteoporosis, osteopenias, bone fractures and bone remodeling surgery.

16 Claims, 3 Drawing Sheets

PUBLICATIONS

Ohmichi et al., "Oxytocin stimulates mitogen–activated protein kinase activity in cultured human puerperal uterine myometrial cells," *Endocrinology*, 136:2082–2087, 1995.

Soloff et al., "Oxytocin receptors: Triggers for parturition and lactation," *Science*, 204:1313–1315, 1979.

Soloff, "Endocrine control of parturition and lactation," In: Wynn RM, Jollie WP (eds) *Biology of the Uterus*, 2nd ed., Plenum Press, NY pp 559–607, 1989.

Strakova and Soloff, "Coupling of oxytocin receptor to G proteins in the rat myometrium during labor: $G_i$ –receptor interaction," *Am J Physiol*, 272:E870–E876, 1997.

Strakova et al., "ERK2 mediates oxytocin–stimulated $PGE_2$ synthesis," *Am J Physiol*, 274:E634–E641, 1998.

Urry et al., "Secondary structure of the cyclic moiety of the peptide hormone oxytocin and its deamino analog," *Proc Natl Acad Sci U S A*, 66(1):111–6, 1970.

Veznik et al., "Regulation of bovine labor with a long–acting carba–analog of oxytocin: a preliminary report," *Am J Vet Res*, 40(3):425–9, 1979.

Williams et al., "Nonpeptide oxytocin antagonists: analogs of L–371,257 with improved potency." *Bioorganic & Medicinal Chemistry Letters*, 9:1311–1316, 1999.

Zingg, "Vasopressin and oxytocin receptors," *In: Baillier's Clinical Endocrinology and Metabolism*, Tindall (ed), 10:75–96, 1996.

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
tgccacccgc tcaagactc                                               19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ggtgatggtg ggttttcc                                                18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ccttcatcgt gtgctggacg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctaggagcag agcacttatg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gtactgccaa tgctcggatg                                              20

<210> SEQ ID NO 6
<211> LENGTH: 20
<212> TYPE: DNA
<213> ORGANISM: Artificial Sequence
<220> FEATURE:

-continued

```
<223> OTHER INFORMATION: Description of Artificial Sequence:  Synthetic
      Primer

<400> SEQUENCE: 6
tgccttcagc ttgtggatgt                                                    20
```

CLINICAL USE OF OXYTOCIN ALONE OR IN COMBINATION TO TREAT BONE DISORDERS

The present application claims the benefit of U.S. Provisional patent application Ser. No. 60/106,134 filed Oct. 29, 1998.

The government owns rights in the present invention pursuant to grant number HD 26168 from the National Institutes of Health.

BACKGROUND OF THE INVENTION

1. Field of the Invention

The present invention relates generally to the fields of medicine and biochemistry. More particularly, it concerns the use of oxytocin or oxytocin analogs either alone or in combination with other agents to treat bone disorders.

2. Description of Related Art

Bone mass increases rapidly during infancy, slowly throughout childhood, and substantially at puberty. At least half of adult bone mass is acquired during the teen years being influenced by genetics, nutrition, sex steroids, and exercise. By early adulthood, bone mass has peaked with loss occurring with aging. Continued bone mineral loss results in reduced bone mass, a condition known as osteopenia. Further decreases lead to osteoporosis, a disruption of normal bone architecture sufficient to produce atraumatic fractures. Osteoporosis generally presents in the elderly population, but also occurs in children and adolescents with chronic illness, malnutrition, or metabolic disorders. Hormone deficiencies, low body weight, anorexia nervosa, exercise associated amenorrhea, delayed puberty and cystic fibrosis are associated with osteopenia in young patients.

Osteoblast cells are responsible for bone mineralization and formation. Calcium, phosphate, magnesium, parathyroid hormone, calcitonin, estrogens, and 1,25 dihydroxyvitamin $D_3$ are important positive regulators of osteoblast function. Bone demineralization and breakdown is carried out by osteoclasts cells, specialized acid secreting cells. The balance between these cells determines the amount of bone formation or breakdown at any given time of life. Osteopenia and osteoporosis are results of dominating osteoclast function causing bone resorption. Other indirect effects increasing bone resorption include inhibition of calcium intestinal absorption (excess glucocorticoids, cystic fibrosis, hyperthyroidism), inhibition of renal hydroxylation of 25-hydroxyvitamin $D_3$ to the active 1,25-dihydroxyvitamin $D_3$ (growth hormone deficiency, cystic fibrosis). Of particular note, no effective means of preventing glucocorticoid related bone loss has been established. Overproduction of glucocorticoids such as in Cushing's disease or prolonged treatment with glucocorticoids for diseases such as juvenile arthritis and childhood leukemias cause substantial bone loss in children.

Osteoporosis is characterized by low bone mass and a disruption of bone architecture that leads to an increased risk of fracture. It occurs in both men and women but most commonly among women following menopause, when the rate of bone resorption becomes greater than that of bone formation. These changes result in progressive bone loss and lead to osteoporosis in a significant proportion of women over age 50. It is estimated that 40% of 50-year-old women will sustain one or more osteoporosis-related fractures of the spine, hip or wrist during their lifetime. Most major pharmaceutical companies, e.g. Glaxo Wellcome, Lily, Merck & Company, Wyeth-Aryst, Schering, etc., are developing compounds for the treatment of osteoporosis because these compounds are indicated for chronic daily use for the rest of an individual's life.

Known functions of oxytocin (OT) include smooth muscle contraction during birth (Soloff, 1989; Fuchs et al., 1982), milk letdown during lactation (Soloff et al., 1979), and prostaglandin release from endometrium/decidua and the amnion (Hinko and Soloff, 1993). These actions occur as very specifically timed events because of the upregulation of oxytocin receptors (OTRs). At term, myometrial OTRs rise just before birth and fall shortly after birth, whereas, OTRs in mammary myoepithelial cells which contract in response to OT release as a reflex to a baby's suckling, increase shortly after birth and remain elevated as long as suckling occurs. From these two examples, it is clear that the rise in OTR levels dictate tissue sensitivity to OT action, and the regulation of OTRs in tissues can be different. To date, known agents that cause an increase in OTR protein levels include estradiol in the uterus (Fuchs et al., 1983; Larcher et al., 1995) and glucocorticoids, and/or agents that elevate intracellular cyclic AMP levels in rabbit amnion (Hinko and Soloff, 1993).

A number of factors stimulate bone growth and differentiation through mechanisms that lead to increased prostaglandin (PG) synthesis. PGs are involved both in osteogenic and osteoclastic responses, and it is through that they are important for bone remodeling (Jee and Ma, 1997). Oxytocin is a potent activator of PG synthesis in the uterine endometrium and amnion (Fuchs et al., 1982; Flint et al., 1986; Moore et al., 1988; Hinko and Soloff, 1992). Although the actions of oxytocin have been regarded to be restricted to specific target cells in the female reproductive tract, mammary gland, and brain nuclei, there is emerging evidence for the presence of oxytocin receptors (OTRs) in other cell types, including thymocytes, fat cells, ovarian cells, and rat insulinomas (Zingg, 1996).

Current competing technologies for the treatment of osteoporosis include estradiol, calcitonin supplemented with dihydroxy Vitamin $D_3$ and calcium, and bisphosphonates. Other therapies are also being developed, as discussed below. Yet, there is a clear need for alternative or synergistic therapeutic regimens for the improved treatment of bone loss associated with osteoporosis and osteopenias.

SUMMARY OF THE INVENTION

The present invention seeks to overcome these problems by providing for a new and novel therapeutic regimen for the treatment of osteoporosis and osteopenias. The present invention concerns methods for treating osteoporosis or osteopenia by formulating an oxytocin receptor stimulator into a pharmaceutically acceptable formulation and administering an amount of the oxytocin receptor stimulator effective to maintain or increase bone formation and/or inhibit bone resorption. In preferred embodiments of the present invention, the oxytocin receptor stimulator is oxytocin. In other embodiments of the present invention, the oxytocin receptor stimulator is an oxytocin analog. The oxytocin analog is selected from the group consisting of 4-threonine-1-hydroxy-deaminooxytocin, 9-Deamidooxytocin, 7-D-proline-oxytocin and its deamino analog, (2,4-Diisoleucine)-oxytocin, deamino oxytocin analog, 1-deamino-1-monocarba-E12-Tyr(OMe)]-OT (dCOMOT), carbetocin, [Thr4-Gly7]-oxytocin (TG-OT), oxypressin, deamino-6-carba-oxytoxin (dC60), L-371,257 and the related series of compounds containing an ortho-trigluoro-ethoxyphenylacetyl core such as L-374,943.

Administration of the oxytocin receptor stimulator may be by any means, including intravenous, intramuscular, nasal, transdermal, oral, intraperitoneal, or bucal administration.

The present invention also concerns methods for treating osteoporosis or osteopenia by formulating an oxytocin receptor stimulator into a pharmaceutically acceptable formulation, administering an amount of the oxytocin receptor stimulator effective to maintain or increase bone formation and/or inhibit bone resorption, and further administering an effective amount of an osteoporosis inhibiting agent. In preferred embodiments, the osteoporosis inhibiting agent is selected from the list comprising an estrogen, antiestrogen, prostaglandin E (PGE), bisphosphonate, calcitonin, 1,25 dihydroxyvitamin D, calcium, growth factors such as growth hormone, insulin, insulin binding growth factor-3 (IGF-BP3), insulin-like growth factor, osteogenic protein-1, transforming growth factor $\beta 1$ (TGF-$\beta 1$) and transforming growth factor $\beta 2$ (TGF-$\beta 2$). nitric oxide, fluoride, or glucocorticoids.

The osteoporosis or osteopenia to be treated in the present invention may be secondary to anorexia nervosa, exercise induced amenorrhea, Turner Syndrome, cystic fibrosis, diabetes mellitus, hyperthyroidism, Cushing's syndrome, glucocorticoid excess, acute lymphoblastic leukemia, Klinefelter's and Kallman's syndromes, alcohol abuse, cigarette smoking, connective tissue disease, osteoarthritis, or rheumatoid arthritis.

The present invention also concerns a method for treating bone loss or accentuating bone healing by formulating an oxytocin receptor stimulator into a pharmaceutically acceptable formulation and administering an amount of the oxytocin receptor stimulator effective to stimulate osteoblast function. In preferred embodiments of the present invention, the oxytocin receptor stimulator is oxytocin. In other embodiments of the present invention, the oxytocin receptor stimulator is an oxytocin analog. The oxytocin analog is selected from the group consisting of 4-threonine-1-hydroxy-deaminooxytocin , 9-Deamidooxytocin, 7-D-proline-oxytocin and its deamino analog, (2,4-Diisoleucine)-oxytocin, deamino oxytocin analog, 1-deamino-1-monocarba-E12-Tyr(OMe)]-OT(dCOMOT), carbetocin, [Thr4-Gly7]-oxytocin (TG-OT), oxypressin, deamino-6-carba-oxytoxin (dC60), L-371,257 and the related series of compounds containing an ortho-trigluoro-ethoxyphenylacetyl core such as L-374,943. Administration of the oxytocin receptor stimulator may be by any means, including intravenous. intramuscular, nasal, transdermal, oral, intraperitoneal, or bucal administration.

The present invention also concerns a method for treating bone loss or accentuating bone healing by formulating an oxytocin receptor stimulator into a pharmaceutically acceptable formulation, administering an amount of the oxytocin receptor stimulator effective to stimulate osteoblast function, and further administering an effective amount of an osteoporosis inhibiting agent. The osteoporosis inhibiting agent is selected from the list comprising an estrogen, antiestrogen, prostaglandin E (PGE), bisphosphonate, calcitonin, 1,25 dihydroxyvitamin D, calcium, growth factors such as growth hormone, insulin, insulin binding growth factor-3 (IGF-BP3), insulin-like growth factor, osteogenic protein-1, transforming growth factor $\beta 1$ (TGF-$\beta 1$) and transforming growth factor $\beta 2$ (TGF-$\beta 2$), nitric oxide, fluoride, or glucocorticoids.

The bone loss to be treated in the present invention may be associated with osteogenesis imperfecta, vitamin D deficiency, bone reconstruction, wound healing, or soft skelatal tissue repair.

The present invention also concerns a method for treating bone loss or accentuating bone healing by formulating an agent that stimulates endogenous oxytocin release into a pharmaceutically acceptable formulation and administering an amount of the agent that stimulates endogenous oxytocin release effective to stimulate osteoblast function. In preffered embodiments, the agent that stimulates endogenous oxytocin release is a relaxin antagonist.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A.) Undifferentiated osteoblastic cells; (FIG. 3B.) differentiated osteoblastic cells; and (FIG. 3C.) Saos-2 cells. Cells were incubated at 37C and treated in the following manner; 100 nM OTA for 1 min, 10 nM OT for 15 min, wash cells 3 times to remove bound antagonist, 10 min recovery, and then 10 nM OT treatment.

(FIG. 4A.) Undifferentiated osteoblastic cells and (FIG. 4B.) differentiated osteoblastic cells. Each point is the mean +/- SE of triplicates. * indicates P<0.05 compared to matched basal control.

DESCRIPTION OF ILLUSTRATIVE EMBODIMENTS

Figure 1:
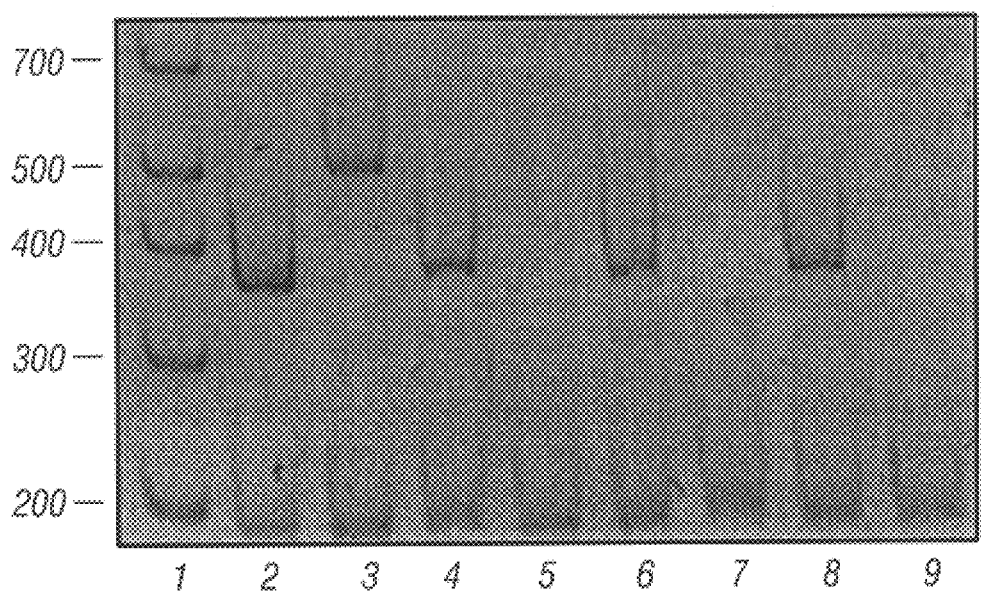
FIG. 1 RT-PCR amplification and DNA analysis of human myometrium (1 $\mu$g) and osteoblastic cells (1 $\mu$g) total RNA. Lane 1 represents the DNA markers. The OTR DNA product (391 bp) from human term myometrium is shown in lane 2 and $V_{1a}R$ DNA product (501 bp) from human term myometrium in lane 3. The OTR DNA product from undifferentiated osteoblastic and differentiated osteoblastic cells and Saos-2 cells are depicted in lanes 4, 6, and 8, respectively. No product for $V_{1a}R$ are demonstrated in undifferentiated and differentiated osteoblastic cells or Saos-2 cells (lanes 5, 7 and 9 respectively). L19 primers were included in each RT-PRT reaction as a control for RT-PCR fidelity (198 bp).

The present invention is based on the novel observation that osteoblasts express functional receptors for oxytocin. Oxytocin binding to oxytocin receptors is demonstrated to stimulate prostaglandin synthesis in osteoblasts. Prostoglandins are involved in osteogenic and osteoclastic responses that are important for bone remodeling. Oxytocin or oxytocin analogs therefore represent a novel therapeutic regimen for the treatment of various bone diseases and for assisting in bone remodeling. Oxytocin and oxytocin analogs can be administered alone or in combination with other agents used to treat bone diseases or aid in bone remodeling. In addition, agents which induce endogenous oxytocin release are also contemplated in the present invention for treatment of bone diseases and for assisting in bone remodeling. The following sections describe oxytocin and its receptor, bone diseases that are contemplated to benefit from the present invention, existing therapies for bone diseases that oxytocin or oxytocin analogs can be administered in combination with, and formulations and routes of administration for agents of the present invention.

I. OXYTOCIN AND OXYTOCIN RECEPTORS

Oxytocin is a short-lived, fast acting hormone, made by the hypothalamus of the brain, along with its close relative vasopressin (anti-diuretic hormone), stored in the posterior pituitary, and released into the blood as needed. It stimulates certain smooth muscle coats, constricts certain blood vessels and facilitates the sensitivity of some tissues to other hormones and nerves. The main tissues affected are the uterus, including endometrium and myometrium, vagina, breasts (both sexes), erectile tissue (both sexes), seminal vesicles, and with special-case effects on uterine muscle contractions in both birth and orgasm, the vascular constriction that lessens placental separation bleeding, and the let-down reflex that nursing mothers have when babies cry.

Oxytocin is produced in two discrete groups of neurons in the brain of all mammals. One group of oxytocin-producing neurons projects to the posterior pituitary, which is an endocrine gland located at the base of the brain. From the pituitary, oxytocin is released into the bloodstream, whereby it exerts the well-known peripheral effects like uterine contraction and milk let-down. The other group of oxytocin-containing neurons projects directly to specific brain areas that are known to mediate maternal behaviors. By acting locally as a chemical messenger in these brain areas, oxytocin acts as a regulator or controller of maternal behaviors.

Agents known to stimulate the release of oxytocin from the posterior pituitary include sensory stimuli arising from the cervix, vagina, and breast. Secretion of oxytocin is also stimulated by increases in the osmality of plasma. Secretion of oxytocin is suppressed by ethanol and ovarian relaxin. The present invention contemplates the use of agents that stimulate the release of endogenous oxytocin, as described above, as well as antagonists of agents that normally suppress the release of endogenous oxytocin.

Oxytocin is currently indicated for stimulation of uterine contraction to induce labor and for the control of postpartum hemorrhage following delivery of the placenta. It is also indicated for stimulation of lactation for breast-feeding. Oxytocin is currently prepared synthetically and sold under various trade names including Pitocin (Parke-Davis, Morris Plains, N.J.) and Syntocinon. It can be administered intravenously, intramuscularly, and by nasal absorption. Activity of oxytocin is expressed in terms of USP units, as defined in a bioassay of uterine-stimulating potency of posterior pituitary extracts. One USP unit is the equivalent of approximately 2 ug of pure peptide.

Oxytocin receptors are expressed on the cell surface membrane, where oxytocin from the circulation or arising from paracrine derived sources, interact and set off a cascade of intracellular events. These events are mediated by G proteins tethered to the intracellular portion of OTRs (Strakova and Soloff, 1997). Subsequent activation of these G proteins result in a rapid rise in intracellular calcium and phosphorylation of MAP kinases (ERK 2). Other events resulting from oxytocin treatment include transcriptional activation of cfos mRNA, a protein vital for cell cycle progression (Strakova et al., 1998).

Oxytocin and oxytocin related compounds, acting through oxytocin receptors, are currently in clinical use for induction of uterine contractions and facilitation of delivery of a baby and placenta at the time of birth. This action is dependent upon the timely increase of OTRs (oxytocin receptors) on the target cell surface. Without an upregulation of OTRs, oxytocin has no action on the parturient uterus, thus limiting adverse side effects.

Examples of oxytocin agonists that would be preferred in the present invention include 4-threonine-1-hydroxy-deaminooxytocin, 9-Deamidooxytocin, an analog of oxytocin containing a glycine residue in place of the glycinamide residue (Ferrier and Du Vigneaud, 1966); 7-D-proline-oxytocin and its deamino analog (Ferraro and Du Vigneaud, 1966); (2,4-Diisoleucine)-oxytocin, an analog of oxytocin with natriuretic and diuretic activities (Hruby et al., 1970); deamino oxytocin analog (Urry et al., 1970); a long-acting oxytocin (OT) analog 1-desamino-1-monocarba-E12-Tyr (OMe)]-OT(dCOMOT) (Veznik et al., 1979; Cort et al., 1982 and 1979); carbetocin, a long-acting oxytocin analog (Hunter et al., 1992); oxytocin agonist [Thr4-Gly7]-oxytocin (TG-OT) (Chadio and Antoni, 1993); oxytocin agonist as described by Olson et al., (1991); oxypressin, an equipotent analog of oxytocin and vasopressin (Gazis et al., 1987); and Deamino-6-carba-oxytoxin (dC60), a potent oxytocin analog considered to be resistant to some of the physiologically significant enzymic systems (Krejci et al, 1981). As well, nonpeptide oxytocin antagonists have been recently been described, which include L-371,257 and the related series of compounds containing an ortho-trigluoro-ethoxyphenylacetyl core (e.g. L-374,943) (Williams et al., 1999). U.S. Pat. No. 5,846,766 relates to a receptor for a posterior pituitary hormone, oxytocin; a DNA sequence encoding for the receptor; a recombinant DNA molecule containing the DNA sequence and a transformant comprising the recombinant DNA molecule. The present invention further relates to methods of detection and diagnosis and a kit to aid in same which comprise either oxytocin, its receptor or antibodies to the receptor.

II. DISEASES AND CONDITIONS REQUIRING STIMULATED BONE GROWTH

The following is a brief discussion of four human conditions to exemplify the variety of diseases and disorders that would benefit from the development of new technology to improve bone repair and healing processes. In addition to the following, several other conditions, such as, for example, vitamin D deficiency; wound healing in general; soft skeletal tissue repair; and cartilage and tendon repair and regeneration, may also benefit from technology concerning stimulated bone growth by oxytocin or oxytocin analogs.

A first, important example is osteoporosis. The term osteoporosis refers to a heterogeneous group of disorders characterized by decreased bone mass and fractures. An estimated 20–25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7–10 billion health care dollars. Demographic trends (i.e., the gradually increasing age of the US population) suggest that these costs may increase 2–3 fold by the year 2020 if a safe and effective treatment is not found. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. Thus, the osteoporotic patient population would benefit from new therapies designed to strengthen bone and speed up the fracture repair process, thus getting these people on their feet before the complications arise.

The second example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would be represent a great advance.

A third example which may benefit from new treatment methods is osteogenesis imperfecta (OI). OI encompasses various inherited connective tissue diseases that involve bone and soft connective tissue fragility in humans (Byers & Steiner, 1992; Prockop, 1990). About one child per 5,000–14,000 born is affected with OI and the disease is associated with significant morbidity throughout life. A certain number of deaths also occur, resulting from the high propensity for bone fracture and the deformation of abnormal bone after fracture repair (OI types II–IV; Bonadio & Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio & Goldstein, 1993). Osteopenia is associated with an increased rate of lone bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II–VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 150 OI mutations have been characterized since 1989 (reviewed in Byers & Steiner, 1992; Prockop, 1990). The vast majority occur in the COL1A1 and COL1A2 genes of type I collagen. Most cases of OI type I appear to result from heterozygous mutations in the COL1A1 gene that decrease collagen production but do not alter primary structure, i.e. heterozygous null mutations affecting COL1A1 expression.

A fourth example is related to bone reconstruction and, specifically, the ability to reconstruct defects in bone tissue that result from traumatic injury; as a consequence of cancer or cancer surgery; as a result of a birth defect, an error in development, or a heritable disorder; or as a result of aging. There is a significant orthopaedic need for more frequent implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al. (1991) have written the "Reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

Other disease states that may benefit from the present invention include osteopenia and osteoporosis arising from other disease states, e.g. anorexia nervosa, exercise induced amenorrhea, Turner Syndrome, cystic fibrosis, diabetes mellitus, hyperthyroidism, Cushing's syndrome, glucocorticoid excess, acute lymphoblastic leukemia, Klinefelter's and Kallman's syndromes, alcohol abuse, cigarette smoking, connective tissue disease, osteoarthritis, and rheumatoid arthritis (*Osleoporosis*, 1994).

III. EXISTING THERAPIES FOR BONE DISEASES

Data bases searched for drugs in use for osteoporosis include Drugdex which is part of the Micromedex Healthcare Series and the 1998 Physicians Desk Reference.

Sandoz provides syntocin injectable intramuscular injections (i.m.) with action beginning within 3–7 minutes and lasting 30–60 minutes and intravenous (i.v.) action begins within seconds and lasts minutes.

Estrogens are used as hormone replacement therapy (HRT) for a number of indications including prevention of bone loss in postmenopausal women. It is know that estradiol acts through a intracellular estrogen receptor that binds to DNA of genes that can then be expressed. It remains uncertain whether estrogens act directly or indirectly in preventing bone loss. It is likely that other agents with similar and/or different mechanisms could replace or work in concert with estrogens/antiestrogens to have positive effects on bone.

Lilly provides raloxifene, an antiestrogen related to tamoxifen with little activity in uterus and breast but estrogenic in osteoblasts. Recently the FDA has approved raloxifene for clinical use. Sandoz provides tamoxifen which is in clinical use.

Bisphosphonates interfere with bone resorption by binding to hydroxyapatite and blocking osteoclast formation, causing an increase in bone formationand bone mass.

Merck & Co.provide alendronate (FOSAMAX)-clinically used. Recommended daily oral doses are 5, 20, and 40 mg for six weeks in postmenopausal women.

Calcitonin which is made of calcitonin/1,25 dihydoxy Vitamin D/Calcium is used for relief of bone pain, Pagets hypercalcemia, postmenopausal osteoporosis (PMO) with calcium and Vitamin $D_3$ supplementation. Other sources of calcitonin include Calcimar injectable (Rhone-Poulanc), Miacalcium injection and miacalcium nasal spray (Sandoz), and calcitonin salmon injection (synthetic) (Astra).

The following compounds are NOT in clinical use but have been tested in vivo or in vitro and demonstrated to have positive effects on bone growth.

Growth Factors/ Cytokine treatment in in vivo animal experiments demonstrate prevention of bone loss with minimal side effects. This evidence strongly supports the use of these compounds in preclinical trials.

TGF-β1/ TGF-β2 affect both bone resorption and bone formation. Subcutaneous injection into rats and mice results in local enhancement of bone formation (Noda and Camilliere, 1989). In cell culture, osteoblast proliferation and the expression of anabolic parameters such as type 1 collagen and alkaline phosphatase are regulated by TGF-β, with both inhibitory and stimulatory effects being reported depending on the experimental conditions and cell type (reviewed in Lern, 1996).

Growth Hormone injections and mild exercise increase the formation and strength of cortical bone in old female rats (Oxlund et al., 1998).

IGF-1/IGF BP-3 effect of systemic administration of insulin-like growth factor-1 on bone formation was potentiated when combined with insulin-like growth factor binding protein-3 (Narusawa et al., 1995).

Osteogenic Protein-1 (OP-1) induces new bone formation in vivo and is synergistic with insulin-like growth factor-1 in stimulating rat osteoblastic cell differentiation and proliferation (Yeh et al., 1997).

Parathyroid Hormone (PTH) causes a dose dependent increase in femoral length and strength in cortical bone in ovariectomized rats (Sato et al., 1997; Dobnig and Turner, 1997).

Neurogenic substance P, a neuropeptide, has wide distribution in central and peripheral nervous system. In vitro treatment of rat osteogenic cells with substance P increased cell proliferation in a dose dependent fashion (Shih and Bernard, 1997).

Prostaglandin $E_2$ stimulates osteoblast (bone formation) proliferation as well as bone resorption depending upon dose and experimental model used (Norrdin et al., 1990). Continuallyadminister prostaglandin $E_2$ or lose effect.

1,25 dihydroxyvitamin $D_3$ is well known with regards to calcium homeostasis, its direct function in bone tissue is currently under investigation. In vivo, administration of high dose Vit. $D_3$ stimulates bone formation (Erben et al., 1997).

Antiestrogens are being developed by many pharmaceutical companies as selective antiestrogens which have estrogenic effects on bone but not estrogenic effects leading to cancer of uterus, ovary, and breast. Some in development include the following:

GW 5638 is an antiestrogen related to tamoxifen with estrogenic activity in bone and antiestrogenic activity in other tissues such as uterus. It is currently under early stages of animal trials (Willson et al., 1997). This compound is being developed by Glaxo Wellcome.

Raloxifene is a modification of the 2-arylbenzothiophene core of raloxifene. Structural variants including 2-cyclohexyl, 2-naphthyl, and 6-carbomethoxy analogs demonstrated efficacy in preventing bone loss in a chronic ovariectomized rat model of postmenopausal osteopenia at doses of 0.1–10 mg/kg body weight (Grese et al., 1997). Eli Lilly and Company are developing these compounds.

CP-336,156 is a new orally active, nonsteroidal, potent estrogen agonist/antagonist that has similar effects in bone as estradiol but without the uterine-stimulating effects associated with estradiol in rats (Ke et al., 1998). This compound is being developed by Pfizer Inc.

No other current technologies compete with oxytocin since these compounds act through mechanisms different than those of oxytocin. In treating osteoporosis, these compounds can either have detrimental side effects e.g. estrogens increase cancer risk or do not effectively treat the disease. Therefore, combinatorial therapy of oxytocin with one or more of these compounds might be indicated.

IV. ROUTES OF ADMINISTRATION AND FORMULATIONS

The broadest application for the use of oxytocin or an oxytocin analog either alone, or in conjunction with the previously mentioned compounds, would be in relation to any bone related disease. There are over 150 known bone disorders. Several means of administering oxytocin can, and have been designed, including a nasal spray, and buccal application.

U.S. Pat. No. 5,763,405 describes a solid pharmaceutical composition for oral administration of small and medium size peptides, particularly vasopressin, oxytocin, and their analogues.

Aqueous compositions of the present invention comprise an effective amount of the oxytocin or oxytocin analog dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an oxytocin or oxytocin analog composition as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An oxytocin or oxytocin analog composition can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active oxytocin or oxytocin analog may be formulated within a therapeutic mixture to comprise about 0.0001 to 1.0 milligrams, or about 0.001 to 0.1 milligrams, or about 0.1 to 1.0 or even about 10 milligrams per dose or so. In preferred embodiments, the active oxytocin or oxytocin analog are formulated within a therapeutic mixture to comprise about 0.001 to about 1 milligram. Multiple doses can also be administered In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used.

Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0. 1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

V. COMBINATION THERAPIES

A major purpose of the invention is to improve the current treatments for bone loss and bone growth. Administration of oxytocin or oxytocin-like compounds alone or in combination with other agents is contemplated. Other agents that can be combined with oxytocin or oxytocin analogs include estrogens/antiestrogens; prostaglandin $E_2$ ($PGE_2$); bisphosphonates; calcitonin; 1,25 dihydroxy vitamin $D_3$; calcium; growth factors [growth hormone, insulin/insulin binding growth factor-3 (IGF-BP3), transforming growth factor B(TGF-B1 and 2)]; nitric oxide; fluoride;glucocorticoids, growth hormone, insulin-like growth factor 1/osteogenic protein-1, etc. that prevent bone loss and/or stimulate bone growth and turnover will improve bone composition under conditions that modify bone quality i.e., bone diseases causing osteopenia, osteoporosis, osteopetrosis, etc. and the breaking of bone.

Various combinations may be employed, oxytocin or an oxytocin analog is "A" and the other agent is "B":

| A/B/A  | B/A/B  | A/A/B | A/B/B | A/B/B/B | B/A/B/B |
|        | B/B/A  |       | B/A/A |         |         |
| B/B/B/A| B/B/A/B| A/A/B/B| A/B/A/B| A/B/B/A| B/B/A/A |
| B/A/B/A| B/A/A/B| A/A/A/B| B/A/A/A| A/B/A/A| A/A/B/A |

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Functional Oxytocin Receptors are Present in Human Osteoblasts

In the present example, the inventors have shown that OTRs are expressed in human bone cells, and that OT stimulates $PGE_2$ synthesis through pathways that could involve increases in $[Ca^{2+}]_i$ as demonstrated in other OT target cell types (Ku et al., 1995; Strakova and Soloff, 1997; Strakova et al., 1998; Ohmichi et al., 1995).

Materials and Methods

Chemicals: Chemicals were obtained from the following sources: OT and OT antagonist (OTA)=[d(CH$_2$)$_5$, Tyr(Me)$^2$, Thr$^4$, Tyr-NH$_2$$^9$] OVT, Peninsula Laboratories (Belmont, Calif.); ascorbic acid, dexamethasone, and β-glycerophosphate, Sigma.

Cell Culture Conditions: Human osteosarcoma cells (Saos-2) cells were obtained from the ATCC (Rockville, Md.). Human osteoblasts (Cheng et al., 1994; Civitelli et al., 1993) were prepared from explants of cultured rib trabecular. These cells were grown in mineralizing media consisting of DMEM supplemented with 10% fetal bovine serum (FBS), 2% penicillin/streptomycin, dexamethasone (100 nM), ascorbate (50 µg/ml, and β3-glycerophosphate (10 µg/ml) in a humidified tissue culture incubator at 37C under an atmosphere of 5% $CO_2$ and 95% air. These conditions accelerate the osteoblastic modulation of undifferentiated human trabecular bone cells and the production of osteogenic mineralizeable collagen matrix (Cheng et al., Civitelli et al., 1993). To retain undifferentiated osteoblastic phenotype, cells were cultured in the absence of dexamethasone, ascorbate, and β-glycerophosphate. Osteoblast phenotype was verified by alkaline phosphatase activity and mineralization of the extracellular matrix using von Kossa staining. The cells were used on the first passage following initial plating.

Determination of OTR ligand binding: OTA was monoiodinated as previously described (Hinko and Soloff, 1992). The specific activity of the iodinated peptide was 2000 Ci/mmol at the time of preparation. Whole cell assays for specific OTR binding activity were performed as described previously, using increasing concentrations of [$^{125}$I]OTA (Copland et al., 1999). Binding studies, each comprised of 9 points, were repeated at least three times. The concentration of cellular DNA was determined in parallel, using the Hoechst dye H 33258 and a Hoefer DyNA Quant fluorometer according to the manufacturer's instructions.

RT-PCR: Total cellular RNA was extracted from cells using guanidine thiocyanate-phenol chloroform and used in reverse transcriptase PCR™ (RT-PCR) as previously described (Copland et al., 1999) Primers had the following sequences:

V$_{1a}$R forward: 5'-TGCCACCCGCTCAAGACTC-3' (SEQ ID NO:1)

V$_{1a}$R reverse: 5'-GGTGATGGTAGGGTTTTCC-3' (SEQ ID NO:2)

OTR forward: 5'-CCTTCATCGTGTGCTGGACG-3' (SEQ ID NO:3)

OTR reverse: 5'-CTAGGAGCAGAGCACTTATG-3' (SEQ ID NO:4)

L19 forward: 5'-GTACTGCCAATGCTCGGATG-3' (SEQ ID NO:5)

L19 reverse: 5'-TGCCTTCAGCTTGTGGATGT-3' (SEQ ID NO:6)

L19, encodes for a ribosomal protein (Davies and Fried, 1995) and was used as a control for each RT-PCR reaction. Correct amplification of primer pairs resulted in a 534 bp product for the human V$_{1a}$ vasopressin receptor (V$_{1a}$R); a 391 bp product for human OTR (OTR); and 198 bp for L19.

Intracellular calcium levels: Real-time recording of $[Ca^{2+}]i$ was performed in single cells using methods and design previously described (Copland et al., 1999). The sensitivity of the assay was 2.5 pg/ml with an intraassay coefficient of variation of 6.3% and the interassay coefficient of variation of 6.9%.

Prostaglandin E2 (PGE2) levels. PGE2 levels in media were measured using a PGE2 enzyme immunoassay (EIA) system from Amersham Life Sciences (Arlington Heights, Ill.) as previously described (Copland, et al., 1999). The sensitivity of the assay was 2.5 pg/ml with an intraassay coefficient of variation of 6.3% and the interassay coefficient of variation of 6.9%.

Statistics: One way analysis of variance followed by Newman-Keuls test were used to determine statistical differences between the means of the different treatment groups (Statview 512 software, BrainPowers, Inc., Calabasas, Calif.). Differences were considered to be significant at P<0.05 level.

Results

Figure 2:
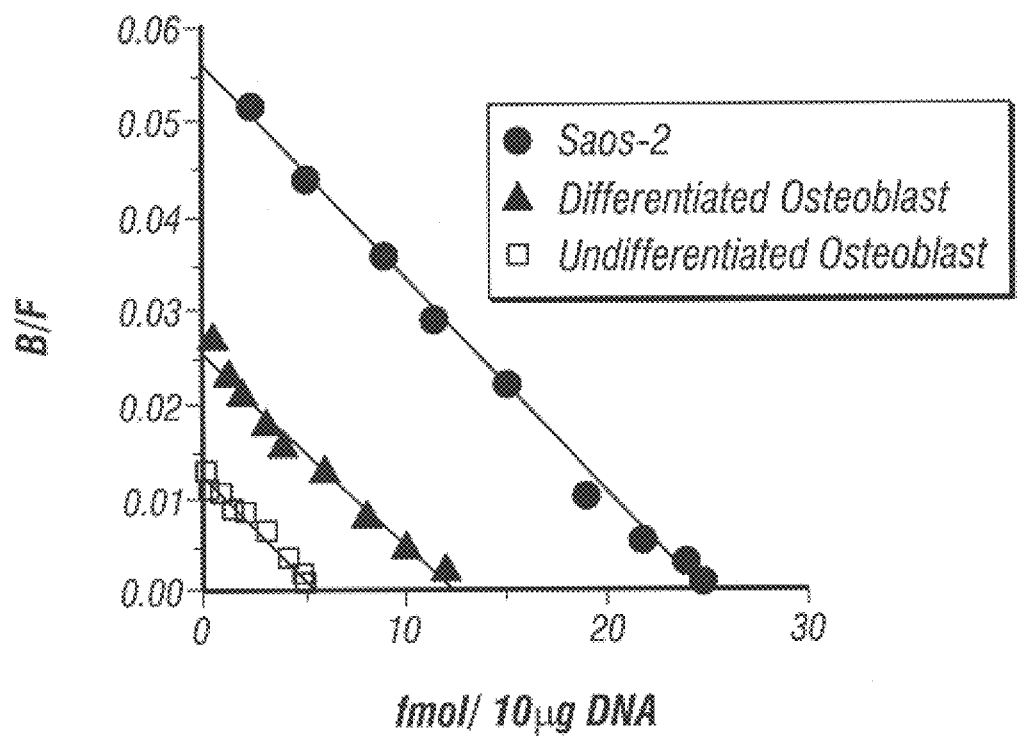
FIG. 2 Scatchard analysis of $^{125}$I-OTA binding to OTR in undifferentiated and differentiated osteoblastic cells and Saos-2 cells.

The inventors first determined whether OTR mRNA was expressed in osteoblastic cells by RT-PCR analysis. Human term myometrium RT-PCR products served as positive controls for OTR (FIG. 1, lane 2) and V$_{1a}$ vasopressin receptor (FIG. 1, lane 3). RT-PCR amplification demonstrated that OTR and mRNA was synthesized by undifferentiated osteoblastic cells (FIG. 1, lane 4), differentiated osteoblasts (FIG. 1, lane 6), and human osteosarcoma Saos-2 cells (FIG. 1, lane 8). The identity of the 391 bp DNA fragment of the OTR was confirmed by DNA sequence analysis to be that of the OTR. Lack of expression of the V$_{1a}$R (FIG. 1, lanes 5, 7 and 9) ruled out OT binding to this receptor. L19 DNA (198 base fragment) was used as a control to demonstrate that the RT-PCR reactions proceeded properly. OTR protein expression was determined by demonstrating high affinity binding (B$_{max}$) with {$^{125}$I]OTA. Scatchard analysis demonstrated a B$_{max}$ of 5.7+/−0.8 (SE) fmol/10 µg DNA and an apparent K$_d$ of 132+/−27 pM for undifferentiated osteoblastic cells and a B$_{max}$ of 12.3+/−1.4 fmol/10 µg DNA and apparent K$_d$ of 175+/−34 pM for differentiated osteoblastic cells (FIG. 2). Saos-2 cells demonstrated a B$_{max}$ of 24.6+/−3.2 fmol/10 µg DNA and apparent K$_d$ of 150+/−28 pM (FIG. 2). The apparent K$_d$ values are comparable with those shown in other OT target cells (Hinko and Soloff, 1992; Copland et al., 1999). Thus, OTR mRNA was transcribed and translated into protein possessing a single class of high affinity binding sites in osteoblast precursor cells, differentiated osteoblast cells, as well as a tumor cell line derived from human osteoblasts.

Figure 3A:
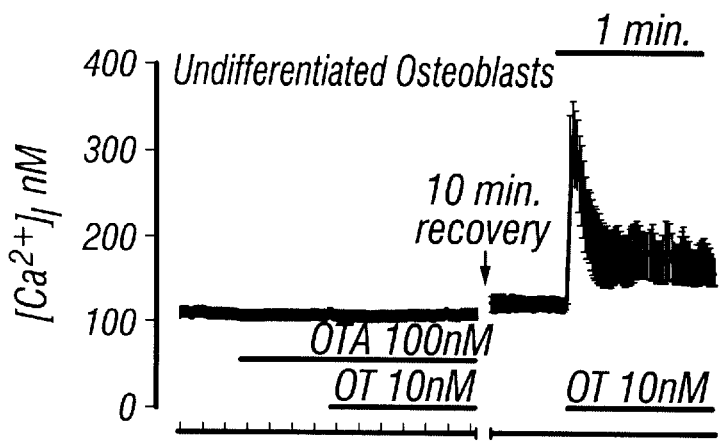
FIG. 3A, FIG. 3B and FIG. 3C Intracellular calcium transients after 10 nM oxytocin treatment.
Figure 3B:
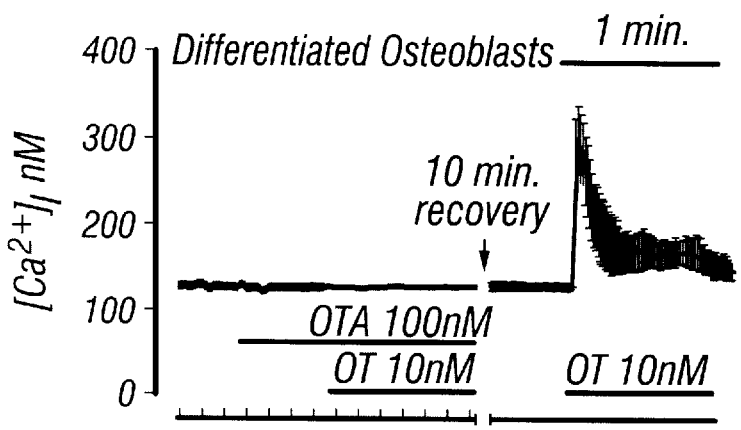
Figure 3C:
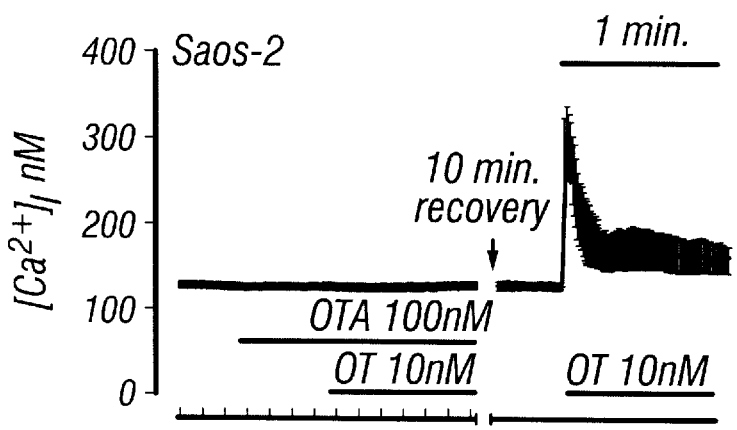

To demonstrate that osteoblast OTRs were functional, the inventors treated cells with 10 nM OT and the concentration of intracellular calcium was measured (FIG. 3). As shown in FIG. 3A, FIG. 3B, and FIG. 3C respectively, undifferentiated osteoblastic cells, differentiated osteoblastic cells, and Saos-2 cells responded within seconds to OT treatment with a rise in $[Ca^{2+}]i$. Oxytocin antagonist, 100 nM, completely blocked the OT induced rise in $[Ca^{2+}]i$. Oxytocin antagonist, 100 nM, completely blocked the OT induced rise in $[Ca^{2+}]i$ in all three cell types (FIG. 3A, FIG. 3B, and FIG. 3C).

Figure 4A:
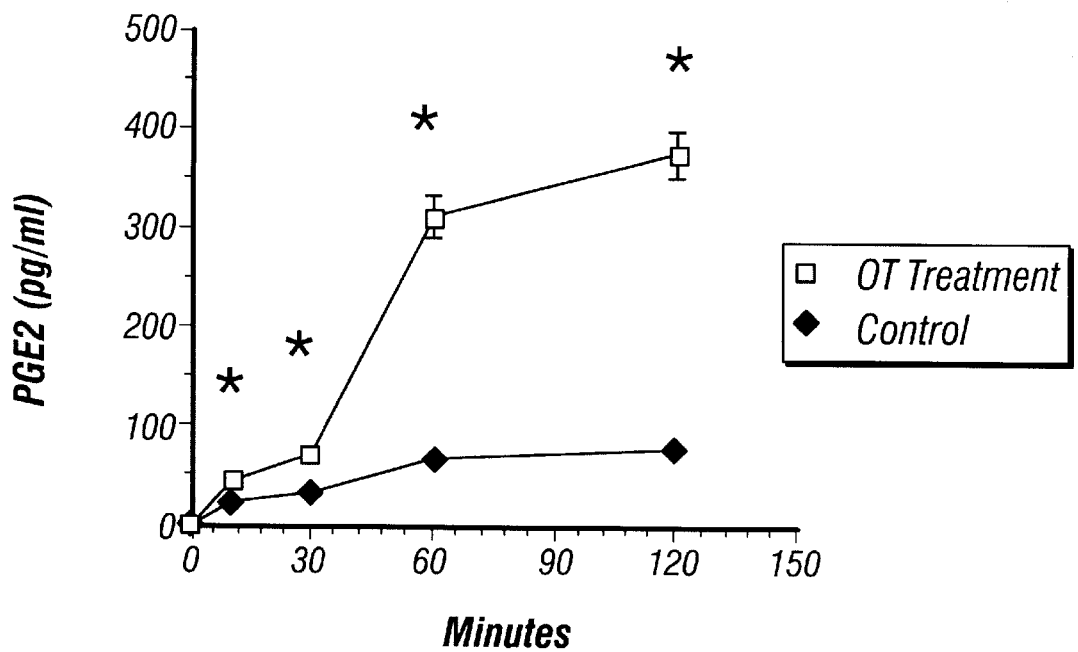
FIG. 4A and FIG. 4B $PGE_2$ levels in media of cells stimulated with 100 nM OT.
Figure 4B:
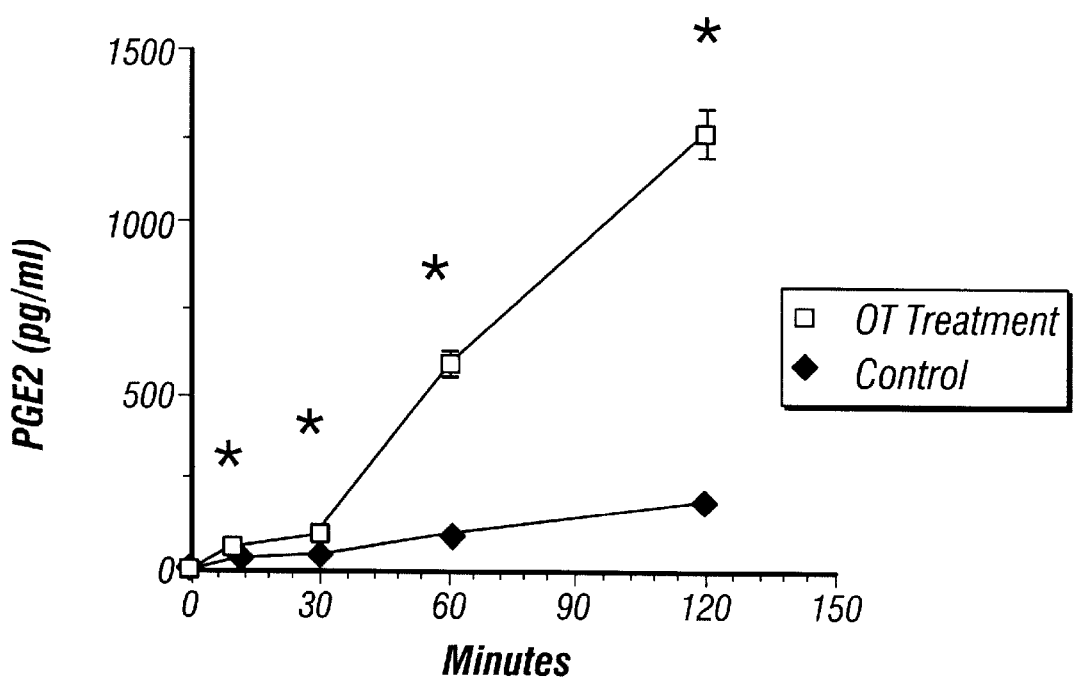

Undifferentiated and differentiated osteoblastic cells were tested to determine whether OT could stimulate $PGE_2$ synthesis. Undifferentiated osteoblastic cells that were allowed to come to confluence and maintained for 2 weeks in either 10% FBS/DMEM or in mineralizing medium (differentiated osteoblast), synthesized and released PGE$_2$ into the media in response to 100 nM OT (FIG. 4A and FIG. 4B, respectively). A 2-fold increase in PGE$_2$ synthesis was demonstrated at 15 and 30 minutes and a 4–6 fold increase in OT-treated over nontreated controls occurred by 1 h of OT stimulation.

Discussion

Undifferentiated or differentiated human trabecular bone cells with osteogenic capacity in primary culture express oxytocin receptors (OTRs). OTR expression then persists upon differentiation to an osteoblast phenotype. A human epithelial osteosarcoma cell line, Saos-2, also expresses OTRs. Expression was determined both at mRNA and protein levels. Functional OTRs are evidenced by an increase in intracellular calcium concentration, $[Ca^{2+}]i$, in response to 10 nM oxytocin (OT). An oxytocin antagonist (OTA) blocked this effect, demonstrating specificity for OT. OT also stimulated prostaglandin E$_2$ (PGE$_2$) synthesis in both confluent undifferentiated and differentiated human trabecular bone cells. This is the first report of OTR mRNA and protein expression and of prescribed OT signal pathways in osteoblastic cells. Since PGE$_2$ has been shown to increase bone turnover in favor of bone formation, OT may be a new class of a bone anabolic agent.

The findings are the first demonstration that human osteoblastic precursor cells, osteoblastic cells, and an osteosarcoma cell line, Saos-2, express OTRs. Furthermore, these OTRs are functional in terms of mediating increases in intracellular calcium levels and PGE$_2$ synthesis. These modalities of OT action have also been associated with bone cell proliferation; prostaglandin plays a key role in achieving a positive bone balance (Jee and Ma, 1997). The link between OT and osteoblast metabolism may extend to other intracellular events known to be induced by OT in other target cells, e.g. MAP kinase phosphorylation and c-Fos expression (Strakova et al., 1998; Ohmichi et al., 1995).

However, because these activities are also essential for the development of osteoclasts as well as osteoblasts, OT could be important in regulating the ontogenetic changes in the balance between osteoblasts and osteoclasts that produce senile and endocrine-mediated osteoporosis. Osteopenias/osteoporosis associated with chronic illness, malnutrition, and metabolic disorders are also possible manifestations of aberrant oxytocin action. The new insight into bone cells as potential OT targets indicates that OT quite possibly plays a physiological role in bone metabolism.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bonadio and Goldstein, "Our understanding of inherited skeletal fragility and what this has taught us about bone structure and function," in Molecular and Cellular Biology of Bone, Noda, M., ed., Academic Press, Inc., San Diego, Calif. pp. 169–189, 1993.

Byers and Steiner, "Osteogenesis imperfecta," *Annu. Rev. Med.* 43:269–289, 1992.

Chadio, Antoni "Specific oxytocin agonist stimulates prolactin release but has no effect on inositol phosphate accumulation in isolated rat anterior pituitary cells," *J Mol Endocrinol* 10(2):107–14, 1993.

Cheng, Yang, Rifas, Zhang, Avioli, "Differentiation of human bone marrow osteogenic stromal cells in vitro: Induction of the osteoblast phenotype by dexamethasone," *Endocrinology*, 134:277–286, 1994.

Civitelli, Beyer, Warlow, Robertson, Geist, Steinberg, "Connexin43 mediates direct intercellular communication in human osteoblastic cell networks," *J Clin. Invest.*, 91:1888–1896, 1993.

Copland, Jeng, Strakova, Ives, Hellmich, Soloff, "Demonstration of functional oxytocin receptors in human breast Hs578T cells and their up-regulation through a PKC-dependent pathway," *Endocrinology*, 140:2258–2267, 1999.

Cort, Einarsson, Astrom "Effect of oxytocin and its long-acting analog on milk let-down and intramammary pressure in healthy lactating sows," *Am J Vet Res* 43(7): 1283–5, 1982.

Cort, Einarsson, Viring "Actions of oxytocin and a long-acting carba oxytocin analog on the porcine myometrium in vitro and in vivo," *Am J Vet Res* 40(3):430–2, 1979.

Davies and Fried, "The L19 ribosomal protein gene (RPL19): gene organization, chromasomal mapping, and novel promoter region," *Genomics*, 25:372–380, 1995.

Dobnig and Turner, "The Effects of programmed administration of human parathyroid hormone fragment (1–34) on bone histomorphometry and serum chemistry in rats," *Endocrinology* 138 :4607–4612, 1997.

Erben, Scutt, Miao, Kollenkirchen, and Haberey, "Short-term treatment of rats with high dose 1,25-dihydroxyvitamin D$_3$ stimulates bone formation and increases the number of osteoblast precursor cells in bone marrow," *Endocrinology* 138:4629–4635, 1997.

Ferraro , Du Vigneaud "7-D-proline-oxytocin and its deamino analog. Diastereoisomers of oxytocin and deamino-oxytocin," *J Am Chem Soc* 88(16):3847–50, 1966.

Ferrier, Du Vigneaud "V9-Deamidooxytocin, an analog of the hormone containing a glycine residue in place of the glycinamide residue," *J Med Chem* 9(1):55–7, 1966.

Flint, Leat, Sheldrick, Stewart, "Stimulation of phosphoinositide hydrolysis by oxytocin and the mechanism by which oxytocin controls prostaglandin synthesis in the ovine endometrium," *Biochem. J.*, 237:797–805, 1986.

Fuchs, Fuchs, Husslein, Soloff, and Fernstrom, "Oxytocin receptors and human parturition. A dual role for oxytocin in the initiation of labor," *Science* 215:1396–1398, 1982.

Gazis, Gonzalez "Mendlowitz M In vivo simultaneous comparison of pressor and uterine responses to a single agonist (oxypressin) in estrous rats," *Can J Physiol Phaimacol* 65(1):6–11, 1987.

Grese, Cho, Finley D R et. al., "Structure-activity relationships of selective estrogen receptor modulators: Modifications to the 2-arylbenzothiophene core of raloxifene," *J Med. Chem.* 40:146–167, 1997.

Hinko and Soloff, "Characterization of oxytocin receptors in rabbit amnion involved in the production of $PGE_2$," *Endocrinology*, 130:3547–3553, 1992.

Hinko and Soloff, "Up-regulation of oxytocin receptors in rabbit amnion by adenosine 3',5'-monophosphate," *Endocrinology* 132:126–132, 1993.

Hinko and Soloff, "Up-regulation of oxytocin receptors in rabbit amnion by glucocorticoids: Potentiation by cyclic adenosine 3',5'- monophosphate," *Endocrinology* 133:1511–1519, 1993.

Hruby, Du Vigneaud, Chan "(2,4-Diisoleucine)-oxytocin. An analog of oxytocin with natriuretic and diuretic activities," *J Med Chem* 13(2):185–7, 1970.

Hunter, Schulz, Wassenaar "Effect of carbetocin, a long-acting oxytocin analog on the postpartum uterus," *Clin Pharmacol Ther* 52(1):60–7, 1992.

In *Osteoporosis*. Marcus R. (ed) Blackwell Scientific Publications, Cambridge, Mass. 1994.

Jee and Ma, "The in vivo anabolic actions of prostaglandins in bone," *Bone*, 21:297–304, 1997.

Ke, Paralkar, Grasser et al., "Effects of CP-336,156, a new, nonsteroidal estrogen agonist/antagonist, on bone, serum cholesterol, uterus, and body composition in rat models," *Endocrinology* 139: 2068–2076, 1998.

Kimura, Takemura, Nomura, Nobunaga, et. al., "Expression of oxytocin receptor in human pregnant myometrium," *Endocrinology* 137:780–785, 1996.

Krejci, Kupkova, Dlabac "Passive avoidance behavior: opposite effects of oxytocin analogs with agonist and antagonist properties," *Regul Pept* 2(5):285–91, 1981.

Ku, Qian, Wen Anwer, Sanborn, "Oxytocin stimulates mymoetrial guanodine triphosphatase and phospholipase-C activities via coupling to Galpha q/l11," *Endocrinology*, 136:1509–1515, 1995.

Lern, "Transforming growth factor-β stimulates bone resorption in neonatal mouse calvariae by a prostaglandin-unrelated but cell proliferation-dependent pathway," *J Bone Miner Res* 11:1628–1639, 1996.

Moore, Dubyak, Moor, Vander, Kooy, "Oxytocin activates the inositol-phopholipid-protein kinase-C system and stimulates prostaglandin production in human amnion cells," *Endocrinology*, 123: 1771–1777, 1988.

Narusawa, Nakamura, Suzuki K et. al., "The effects of recombinant human insulin-like growth factor (rhIGF)-1 and rhIGF-1/IGF binding protein-3 administration on rat osteopenia induced by ovariectomy with concomitant bilateral sciatic neurectomy," *J Bone Miner Res* 10: 1853–1864, 1995.

Noda and Camilliere, "In vivo stimulation of bone formation by transforming growth factor β," *Endocrinology* 124:2991–2994, 1989.

Norrdin, Jec, and High, "The role of prostaglandins in bone in vivo," *Prostaglandins, Leukotrienes, and Essential Fatty Acids* 41:139–149, 1990.

Ohmichi, Koike, Nohara, Kanda, Sakamoto, Zhang, Hirota, Miyake, "Oxytocin stimulates mitogen-activated protein kinase activity in cultured human puerperal uterine myometrial cells," *Endocrinology*, 136:2082–2087, 1995.

Olson, Drutarosky, Chow, Hruby, Stricker, Verbalis "Oxytocin and an oxytocin agonist administered centrally decrease food intake in rats," *Peptides* 12(1):113–8, 1991.

Oxlund, Andersen, Orskov, and Andreassen, "Growth hormone and mild exercise in combination markedly enhance cortical bone formation and strength in old rats," *Endocrinology* 139:1899–1904, 1998.

Prockop, "Mutations that alter the primary structure of type I collagen. The perils of a system for generating large structures by the principle of nucleated growth," *J. Biol. Chem.* 265:15349–15352, 1990.

Sato, Zeng, Turner, "Biosynthetic human parathyroid hormone (1–34) effects on bone quality in aged ovariectomized rats," *Endocrinology* 138:4330–4337, 1997.

Shih and Bernard, "Neurogenic substance P stimulates osteogenesis in vitro," *Peptides* 18:323–326, 1997.

Soloff, "Endocrine control of parturition," In:Wynn R M, Jollie WP (eds) *Biology of the Uterus*, 2nd ed., Plenum Press, NY pp 559–607, 1989.

Soloff, Alexandrova, and Fernstrom. Oxytocin receptors: Triggers for parturition and lactation? *Science* 204: 1313–1315, 1979.

Strakova and Soloff, "Coupling of oxytocin receptor to G proteins in the rat myometrium during labor: $G_i$-receptor interaction," *Am J Physiol* 272:E870–E876, 1997.

Strakova, Copland, Lolait, and Soloff, "ERK2 mediates oxytocin-stimulated PGE synthesis," *Am J Physiol* 274:E634–E641, 1998.

Toriumi et al., *Arch. Otolaryngol Head Neck Surg.*, 117:1101–1112, 1991.

Urry, Ohnish, Walter "Secondary structure of the cyclic moiety of the peptide hormone oxytocin and its deamino analog," *Proc Natl Acad Sci USA* 66(1): 111–6, 1970.

Veznik, Holub, Zraly, Kummer, Holcak, Jost, Cort "Regulation of bovine labor with a long-acting carba-analog of oxytocin: a preliminary report," *Am J Vet Res* 40(3):425–9, 1979.

Williams, Bock Evans, Freidinger, et al. "Nonpeptide oxytocin antagonists: analogs of L-371,257 with improved potency." *Bioorganic & Medicinal Chemistry Letters* 9:1311–1316, 1999.

Willson and Norris, Wagner BL et. al., "Dissection of the molecular mechanism of action of GW5638, a novel estrogen receptor ligand, provides insights into the role of estrogen receptor in bone," *Endocrinology* 138:3901–3911, 1997.

Yeh, Adamo, Olson, and Lee, "Osteogenic protein-I and insulin-like growth factor 1 synergistically stimulate rat osteoblastic cell differentiation and proliferation," *Endocrinology* 138:4181–4190, 1997.

Zingg, "Vasopressin and oxytocin receptors," In: *Baillier's Clinical Endocrinilogy and Metabolism*, Tindall (ed), 10:75–96, 1996.

What is claimed is:

1. A method for treating osteoporosis or osteopenia comprising:
   (a) formulating an oxytocin receptor stimulator into a pharmaceutically acceptable formulation; and
   (b) administering an amount of said oxytocin receptor stimulator effective to maintain or increase bone formation and/or inhibit bone resorption.

2. The method of claim 1, wherein the oxytocin receptor stimulator is oxytocin.

3. The method of claim 1, wherein the oxytocin receptor stimulator is an oxytocin analog.

4. The method of claim 3, wherein the oxytocin analog is selected from the group consisting of 4-threonine-1-hydroxy-deaminooxytocin, 9-Deamidooxytocin, 7-D-proline-oxytocin and its deamino analog, (2,4-Diisoleucine)-oxytocin and its deamino oxytocin analog, 1-desamino-1-monocarba-E12-Tyr(OMe)-OT, carbetocin, [Thr4-Gly7]-oxytocin, oxypressin, deamino-6-carba-oxytoxin, L-371,257 and of compounds containing an ortho-trigluoro-ethoxyphenylacetyl core such as and analog thereof.

5. The method of claim 1, wherein said administering is intravenous, intramuscular, nasal, transdermal, oral, intraperitoneal, or bucal.

6. The method of claim 1, further comprising administering an effective amount of an osteoporosis inhibiting agent.

7. The method of claim 6, wherein the osteoporosis inhibiting agent is selected from the list comprising an estrogen, antiestrogen, prostaglandin E, bisphosphonate, calcitonin, 1,25 dihydroxyvitamin D, calcium, growth factors selected from the group consisting of growth hormone, insulin, insulin binding growth factor-3, insulin-like growth factor, osteogenic protein-1, transforming growth factor $\beta 1$ and transforming growth factor $\beta 2$, nitric oxide, fluoride, or glucocorticoids.

8. The method of claim 1, wherein the osteoporosis or osteopenia is secondary to anorexia nervosa, exercise induced amenorrhea, Turner Syndrome, cystic fibrosis, diabetes mellitus, hyperthyroidism, Cushing's syndrome, glucocorticoid excess, acute lymphoblastic leukemia, Klinefelter's and Kallman's syndromes, alcohol abuse, cigarette smoking, connective tissue disease, osteoarthritis, or rheumatoid arthritis.

9. A method for treating bone loss or accentuating bone healing comprising:
   (a) formulating an oxytocin receptor stimulator into a pharmaceutically acceptable formulation; and
   (b) administering an amount of said oxytocin receptor stimulator effective to stimulate osteoblast function.

10. The method of claim 9, wherein the oxytocin receptor stimulator is oxytocin.

11. The method of claim 9, wherein the oxytocin receptor stimulator is an oxytocin analog.

12. The method of claim 9, wherein said administering is intravenous, intramuscular, nasal, transdermal, oral, intraperitoneal, or bucal.

13. The method of claim 9, further comprising administering an effective amount of an osteoporosis inhibiting agent.

14. The method of claim 13, wherein the osteoporosis inhibiting agent is selected from the list comprising an estrogen, antiestrogen, prostaglandin E, bisphosphonate, calcitonin, 1,25 dihydroxyvitamin D, calcium, growth factors such as growth hormone, insulin, insulin binding growth factor-3, insulin-like growth factor, osteogenic protein-1, transforming growth factor $\beta 1$ and transforming growth factor $\beta 2$, nitric oxide, fluoride, or glucocorticoids.

15. The method of claim 9, wherein the bone loss is associated with osteogenesis imperfecta, vitamin D deficiency, bone reconstruction, wound healing, or soft skelatal tissue repair.

16. A method for treating bone loss or accentuating bone healing comprising:
   (a) formulating an agent that stimulates endogenous oxytocin release into a pharmaceutically acceptable formulation; and
   (b) administering an amount of said agent that stimulates endogenous oxytocin release effective to stimulate osteoblast function.

\* \* \* \* \*

UNITED STATES PATENT AND TRADEMARK OFFICE
CERTIFICATE OF CORRECTION

PATENT NO. : 6,333,313 B1 Page 1 of 1
DATED : December 25, 2001
INVENTOR(S) : Copland, III et al.

It is certified that error appears in the above-identified patent and that said Letters Patent is hereby corrected as shown below:

<u>Column 23,</u>
Lines 30-32, please delete "of compounds containing an ortho-trigluoro-ethoxyphenylacetyl core such as and analog" and insert -- analogs -- therefor.
Line 45, please delete "or" and insert -- and -- therefor.

<u>Column 24,</u>
Line 12, please delete "tissuc" and insert -- tissue -- therefor.
Line 34, please delete "such as" and insert -- selected from the group consisting of -- therefor.
Line 41, please delete "skelatal" and insert -- skeletal -- therefor.

Signed and Sealed this

Twenty-fourth Day of September, 2002

Attest:

Attesting Officer

JAMES E. ROGAN
Director of the United States Patent and Trademark Office